United States Patent
Liu et al.

(10) Patent No.: US 10,465,198 B2
(45) Date of Patent: Nov. 5, 2019

(54) RECOMBINANT BACILLUS SUBTILIS FOR INCREASING PRODUCTION OF ACETYLGLUCOSAMINE AND CONSTRUCTION METHOD THEREOF

(71) Applicant: Jiangnan University, Wuxi (CN)

(72) Inventors: Long Liu, Wuxi (CN); Jianghua Li, Wuxi (CN); Tengfei Niu, Wuxi (CN); Jian Chen, Wuxi (CN); Guocheng Du, Wuxi (CN)

(73) Assignee: JIANGNAN UNIVERSITY, Wuxi, Jiangsu (CN)

( * ) Notice: Subject to any disclaimer, the term of this patent is extended or adjusted under 35 U.S.C. 154(b) by 0 days.

(21) Appl. No.: 15/847,987

(22) Filed: Dec. 20, 2017

(65) Prior Publication Data

US 2019/0144875 A1 May 16, 2019

(30) Foreign Application Priority Data

Nov. 15, 2017 (CN) .......................... 2017 1 1126127

(51) Int. Cl.
| | |
|---|---|
| C12N 15/75 | (2006.01) |
| C12N 1/20 | (2006.01) |
| C12R 1/125 | (2006.01) |
| C12N 9/90 | (2006.01) |
| C12N 9/12 | (2006.01) |
| C12P 19/28 | (2006.01) |
| C07H 5/06 | (2006.01) |
| C12N 9/10 | (2006.01) |

(52) U.S. Cl.
CPC .............. *C12N 15/75* (2013.01); *C07H 5/06* (2013.01); *C12N 1/20* (2013.01); *C12N 9/1096* (2013.01); *C12N 9/1205* (2013.01); *C12N 9/90* (2013.01); *C12P 19/28* (2013.01); *C12R 1/125* (2013.01); *C12Y 206/01016* (2013.01); *C12Y 207/01011* (2013.01); *C12Y 503/01009* (2013.01); *C12Y 504/0201* (2013.01); *C12N 2310/12* (2013.01)

(58) Field of Classification Search
None
See application file for complete search history.

(56) References Cited

PUBLICATIONS

Liu et al. (Metab Eng. (2013) 19:104-115). (Year: 2013).*
Niu et al. (ACS Synth. Biol. (2018) 7(10):2423-2435). (Year: 2018).*

* cited by examiner

*Primary Examiner* — J. E. Angell
(74) *Attorney, Agent, or Firm* — IPro, PLLC; Na Xu

(57) ABSTRACT

The invention discloses a method for improving the yield of *Bacillus subtilis* acetylglucosamine, which belongs to the technical field of genetic engineering. In the invention, the recombinant *Bacillus subtilis* S5 (S5-PxylA-glmS-P43-GNA1) is taken as a starting strain, and the glmS ribozyme is integrated into the mid of rbs and the promoter sequence of the glmM and pfkA gene, respectively. The ribozyme mutant has the advantage of prolonging the stability of the mRNA and integrated into the mid of rbs and the promoter sequence of the pgi gene. The yield of GlcNAc of the recombinant strain reaches 11.79-20.05 g/L. This laid the foundation for the further metabolic engineering of *Bacillus subtilis* to produce GlcNAc.

9 Claims, 2 Drawing Sheets
Specification includes a Sequence Listing.

SEQUENCE LISTING

```
<160> NUMBER OF SEQ ID NOS: 26

<210> SEQ ID NO 1
<211> LENGTH: 210
<212> TYPE: DNA
<213> ORGANISM: Artificial Sequence
<220> FEATURE:
<223> OTHER INFORMATION: Synthetic DNA

<400> SEQUENCE: 1
gctttaccta taattatccc gcccgaacta agcgcccgga aaaaggctta gttgacgagg      60
atggaggtta tcgaattttc ggcggatgcc tcccggctga gtgtgcagat cacagccgta     120
aggatttctt caaaccaagg gggtgactcc ttgaacaaag agaaatcaca tgatcttcca     180
aaaaacatgt aggaggggac gattgaaagt                                      210

<210> SEQ ID NO 2
<211> LENGTH: 52
<212> TYPE: DNA
<213> ORGANISM: Artificial Sequence
<220> FEATURE:
<223> OTHER INFORMATION: Synthetic DNA

<400> SEQUENCE: 2
```
gcatacatta tacgaacggt agagcttgtc ttgttcttat tttctcaata gg          52

<210> SEQ ID NO 3
<211> LENGTH: 52
<212> TYPE: DNA
<213> ORGANISM: Artificial Sequence
<220> FEATURE:
<223> OTHER INFORMATION: Synthetic DNA

<400> SEQUENCE: 3
ttctccattc acctcagcaa caagattgta aaaggagacg aagaaagtca aa           52

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA

<400> SEQUENCE: 4
cgaacacctg tttaccgact t                                             21

<210> SEQ ID NO 5
<211> LENGTH: 53
<212> TYPE: DNA
<213> ORGANISM: Artificial Sequence
<220> FEATURE:
<223> OTHER INFORMATION: Synthetic DNA

<400> SEQUENCE: 5
gctatacgaa cggtagaatc tcccctcagc aacatatatg attaaacata aca          53

<210> SEQ ID NO 6
<211> LENGTH: 52
<212> TYPE: DNA
<213> ORGANISM: Artificial Sequence
<220> FEATURE:
<223> OTHER INFORMATION: Synthetic DNA

<400> SEQUENCE: 6
tttgactttc ttcgtctcct tttacaatct tgttgctgag gtgaatggag aa           52

<210> SEQ ID NO 7
<211> LENGTH: 23
<212> TYPE: DNA
<213> ORGANISM: Artificial Sequence
<220> FEATURE:
<223> OTHER INFORMATION: Synthetic DNA

<400> SEQUENCE: 7
aatactgtgc ttcttgccgc gtt                                           23

<210> SEQ ID NO 8
<211> LENGTH: 53
<212> TYPE: DNA
<213> ORGANISM: Artificial Sequence
<220> FEATURE:
<223> OTHER INFORMATION: Synthetic DNA

<400> SEQUENCE: 8
tgttatgttt aatcatatat gttgctgagg ggagattcta ccgttcgtat agc          53

<210> SEQ ID NO 9
<211> LENGTH: 52
<212> TYPE: DNA

```
<213> ORGANISM: Artificial Sequence
<220> FEATURE:
<223> OTHER INFORMATION: Synthetic DNA

<400> SEQUENCE: 9
cctattgaga aataagaac aagacaagct ctaccgttcg tataatgtat gc          52

<210> SEQ ID NO 10
<211> LENGTH: 52
<212> TYPE: DNA
<213> ORGANISM: Artificial Sequence
<220> FEATURE:
<223> OTHER INFORMATION: Synthetic DNA

<400> SEQUENCE: 10
gcatacatta tacgaacggt agagcttgtc ttgttcttat tttctcaata gg          52

<210> SEQ ID NO 11
<211> LENGTH: 67
<212> TYPE: DNA
<213> ORGANISM: Artificial Sequence
<220> FEATURE:
<223> OTHER INFORMATION: Synthetic DNA

<400> SEQUENCE: 11
cttgcccatt ttataatcgc ttcctcctaa gattgtaaga ttgtaaaagg agacgaagaa  60
agtcaaa                                                           67

<210> SEQ ID NO 12
<211> LENGTH: 21
<212> TYPE: DNA
<213> ORGANISM: Artificial Sequence
<220> FEATURE:
<223> OTHER INFORMATION: Synthetic DNA

<400> SEQUENCE: 12
aaattgaacg gacaggaagc c                                           21

<210> SEQ ID NO 13
<211> LENGTH: 43
<212> TYPE: DNA
<213> ORGANISM: Artificial Sequence
<220> FEATURE:
<223> OTHER INFORMATION: Synthetic DNA

<400> SEQUENCE: 13
gctatacgaa cggtagaatc tccttattcc gatgaggatt gtg                   43

<210> SEQ ID NO 14
<211> LENGTH: 67
<212> TYPE: DNA
<213> ORGANISM: Artificial Sequence
<220> FEATURE:
<223> OTHER INFORMATION: Synthetic DNA

<400> SEQUENCE: 14
tttgactttc ttcgtctcct tttacaatct tacaatctta ggaggaagcg attataaaat  60
gggcaag                                                           67

<210> SEQ ID NO 15
<211> LENGTH: 22
<212> TYPE: DNA
<213> ORGANISM: Artificial Sequence
<220> FEATURE:
<223> OTHER INFORMATION: Synthetic DNA
```

<400> SEQUENCE: 15
caagaccgag atccgcgttt tt    22

<210> SEQ ID NO 16
<211> LENGTH: 43
<212> TYPE: DNA
<213> ORGANISM: Artificial Sequence
<220> FEATURE:
<223> OTHER INFORMATION: Synthetic DNA

<400> SEQUENCE: 16
cacaatcctc atcggaataa ggagattcta ccgttcgtat agc    43

<210> SEQ ID NO 17
<211> LENGTH: 52
<212> TYPE: DNA
<213> ORGANISM: Artificial Sequence
<220> FEATURE:
<223> OTHER INFORMATION: Synthetic DNA

<400> SEQUENCE: 17
cctattgaga aaataagaac aagacaagct ctaccgttcg tataatgtat gc    52

<210> SEQ ID NO 18
<211> LENGTH: 47
<212> TYPE: DNA
<213> ORGANISM: Artificial Sequence
<220> FEATURE:
<223> OTHER INFORMATION: Synthetic DNA

<400> SEQUENCE: 18
gcatacatta tacgaacggt aggctttacc tataattatc ccgcccg    47

<210> SEQ ID NO 19
<211> LENGTH: 50
<212> TYPE: DNA
<213> ORGANISM: Artificial Sequence
<220> FEATURE:
<223> OTHER INFORMATION: Synthetic DNA

<400> SEQUENCE: 19
gtcattgctt gtccctccat aacggacttt caatcgtccc ctcctacatg    50

<210> SEQ ID NO 20
<211> LENGTH: 25
<212> TYPE: DNA
<213> ORGANISM: Artificial Sequence
<220> FEATURE:
<223> OTHER INFORMATION: Synthetic DNA

<400> SEQUENCE: 20
ggttgacatg atgagccacg tattc    25

<210> SEQ ID NO 21
<211> LENGTH: 58
<212> TYPE: DNA
<213> ORGANISM: Artificial Sequence
<220> FEATURE:
<223> OTHER INFORMATION: Synthetic DNA

<400> SEQUENCE: 21
gctatacgaa cggtagaatc tccccataac ggtataatgt tttcatcttt cactttat    58

<210> SEQ ID NO 22

```
<211> LENGTH: 50
<212> TYPE: DNA
<213> ORGANISM: Artificial Sequence
<220> FEATURE:
<223> OTHER INFORMATION: Synthetic DNA

<400> SEQUENCE: 22
catgtaggag gggacgattg aaagtccgtt atggagggac aagcaatgac            50

<210> SEQ ID NO 23
<211> LENGTH: 25
<212> TYPE: DNA
<213> ORGANISM: Artificial Sequence
<220> FEATURE:
<223> OTHER INFORMATION: Synthetic DNA

<400> SEQUENCE: 23
ctgacagcaa tcggcaagag accta                                       25

<210> SEQ ID NO 24
<211> LENGTH: 58
<212> TYPE: DNA
<213> ORGANISM: Artificial Sequence
<220> FEATURE:
<223> OTHER INFORMATION: Synthetic DNA

<400> SEQUENCE: 24
ataaagtgaa agatgaaaac attataccgt tatggggaga ttctaccgtt cgtatagc   58

<210> SEQ ID NO 25
<211> LENGTH: 47
<212> TYPE: DNA
<213> ORGANISM: Artificial Sequence
<220> FEATURE:
<223> OTHER INFORMATION: Synthetic DNA

<400> SEQUENCE: 25
cgggcgggat aattataggt aaagcctacc gttcgtataa tgtatgc               47

<210> SEQ ID NO 26
<211> LENGTH: 171
<212> TYPE: DNA
<213> ORGANISM: Artificial Sequence
<220> FEATURE:
<223> OTHER INFORMATION: Synthetic DNA

<400> SEQUENCE: 26
cctataatta tagcgcccga actaagcgcc cggaaaaagg cttagttgac gaggatggag    60
gttatcgaat tttcggcgga tgcctcccgg ctgagtgtgc agatcacagc cgtaaggatt   120
tcttcaaacc aaggggtga ctccttgaac aaagagaaat cacatgatct t             171
```

RECOMBINANT BACILLUS SUBTILIS FOR INCREASING PRODUCTION OF ACETYLGLUCOSAMINE AND CONSTRUCTION METHOD THEREOF

TECHNICAL FIELD

The disclosure herein relates to the field of genetic engineering, and more particularly to a recombinant *Bacillus subtilis* for producing acetylglucosamine and construction method thereof.

BACKGROUND

GlcNAc is a pharmaceutically and nutraceutically useful compound, which was widely used for treatment of osteoarthritis and maintaining health of the joint. Previously a *Bacillus subtilis* strain has been constructed for efficient production of GlcNAc. However, low GlcNAc titer in industrial relevant fermentation medium of engineered *B. subtilis* restricts the application for industrial production. To move a step forward for microbial GlcNAc fermentation in industrial conditions, yield and GlcNAc titer should be enhanced. The glmS ribozyme can cleave the messenger RNA of the glmS gene in Gram-positive bacteria. It is activated by glucosamine-6-phosphate (GlcN6P) which is the metabolic product of the GlmS enzyme to stimulate autocatalytic site-specific cleavage. The metabolite-induced self-cleavage specifically targets the downstream transcript for intracellular degradation. This degradation pathway relies on action of Rnase J1. Rnase J1 specifically degrades products with a 5' hydroxyl terminal arisen from site-specific cleavage. And the ribozyme serves as a metabolite-responsive genetic switch that represses the glmS gene in response to rising glucosamine-6-phosphate (GlcN6P) concentrations. GlcNAc related biosynthesis was divided into modules including into the GlcNAc synthesis module, pentose phosphate pathway (PPP) module, glycolysis module, and peptidoglycan synthesis module. The GlcNAc synthesis module, peptidoglycan synthesis module, glycolysis module and pentose phosphate pathway module compete for the same precursors. Therefore, the competitive glycolysis and peptidoglycan synthesis modules should be downregulated and the GlcNAc synthesis module should be upregulated for GlcNAc synthesis. As implied above, most methods for metabolic engineering (esp. in *B. subtilis*) impart an inherently static control of gene expression, and thus result in undesirable and unbalanced metabolic flux distributions. As a result, titers are often limited due to toxic intermediates and metabolic imbalances.

SUMMARY

The first goal of the present invention is to provide a recombinant *Bacillus subtilis* for producing acetylglucosamine, wherein the recombinant *Bacillus subtilis* dynamically regulate glmM, pfkA and pgi expression using the glmS ribozyme and/or the glmS ribozyme mutant.

In one embodiment of the present invention, the wherein said recombinant *Bacillus subtilis* dynamically upregulate pgi expression using the glmS ribozyme mutant (cleavage site AG→CC).

In one embodiment of the present invention, the glmS ribozyme responds linearly to increases in GlcN6P concentrations, and the half-life of the precursor RNA is reduced by saturation of the ribozyme with the ligand from approximately 4 h to less than 15 s. For endogenous systems, feedback regulation of glmS ribozyme sRNA plays an important role in fine-tuning the expression of pfkA and glmM.

In one embodiment of the present invention, the wherein said recombinant *Bacillus subtilis* dynamically enhanced the inhibition on pfkA and glmM under relatively higher GlcN6P concentrations; and attenuated the inhibition on pfkA and glmM under relatively lower GlcN6P concentrations In one embodiment of the present invention, the invention provides a recombinant *Bacillus subtilis* for producing acetylglucosamine, wherein the recombinant *Bacillus subtilis* is obtained by homologous recombination to integrate glmS ribozyme gene of *Bacillus subtilis* into the genome between the promoter and rbs of glmM and pfkA, respectively, and integrate glmS ribozyme mutant into the genome between the promoter and rbs of pgi.

In one embodiment of the present invention, the strain *Bacillus subtilis* was used as a host.

In one embodiment of the present invention, the strain *Bacillus subtilis* 168 was used as a host.

In one embodiment of the present invention, the gene encoding glmS ribozyme is shown in SEQ ID NO.26.

In one embodiment of the present invention, the gene encoding the mutant of glmS ribozyme is shown in SEQ ID NO.1.

In one embodiment of the present invention, the wherein said recombinant *Bacillus subtilis* is *Bacillus subtilis* SFMI, which is obtained by homologous recombination to integrate glmS ribozyme gene of *Bacillus subtilis* into the genome between the promoter and rbs of glmM and pfkA, respectively, and integrate glmS ribozyme mutant into the genome between the promoter and rbs of pgi.

In one embodiment of the present invention, the the construction method comprises following steps:

(1) constructing a integrating cassette of a glmS ribozyme encoding gene, wherein the integrating cassette includes glmM upstream homologous fragment, a resistance gene spc, glmS ribozyme encoding gene fragment and glmM downstream homologous fragment; and transforming the integrating cassette into *Bacillus subtilis*, to obtain the recombinant *Bacillus subtilis* through screening and PCR validation.

(2) constructing a integrating cassette of a glmS ribozyme encoding gene, wherein the integrating cassette includes pfkA upstream homologous fragment, a resistance gene spc, glmS ribozyme encoding gene fragment and pfkA downstream homologous fragment; and transforming the integrating cassette into *Bacillus subtilis*, to obtain the recombinant *Bacillus subtilis* through screening and PCR validation.

(3) constructing a integrating cassette of a glmS ribozyme mutant encoding gene, wherein the integrating cassette includes pgi upstream homologous fragment, a resistance gene spc, glmS ribozyme mutant encoding gene fragment and pgi downstream homologous fragment; and transforming the integrating cassette into *Bacillus subtilis*, to obtain the recombinant *Bacillus subtilis* through screening and PCR validation.

The second goal of the present invention is to provide a method of acetylglucosamine production, which is carried out using the wherein said recombinant *Bacillus subtilis*.

In one embodiment of the present invention, the method is carried out by inoculating the recombinant *Bacillus subtilis* into the fermentation culture medium.

In one embodiment of the present invention, the method is carried out by inoculating the recombinant *Bacillus subtilis* into the fermentation culture medium, and then incubated at 37° C. for 72 hours.

In one embodiment of the present invention, the fermentation medium comprises (g/L): glucose 100.0, $KH_2PO_4$ 2.5, $K_2HPO_4$ 12.5, $(NH_4)_2SO_4$ 6.0, tryptophan 6.0, yeast abstract 12.0, $MgSO_4$ 3.0, and 10 mL/L trace element solution.

In one embodiment of the present invention, trace element solution comprises (g/L): $MnSO_4$ 1.0, $CoCl_2$ 0.4, $Na_2MoO_4$ 0.2, $ZnSO_4$ 0.2, $AlCl_3$ 0.1, $CuCl_2$ 0.1, Boric Acid 0.05.

Benefit: in this invention, the recombinant *Bacillus subtilis* can use the glmS ribozyme self-regulate the expression of glmM and pfkA in response to GlcN6P, and glmS ribozyme mutant increase the expression of pgi. In the invention, the strategy increase acetylglucosamine to 20.05 g/L, which is increased by 63.9% compared with the original strain. Here the developed strategy can be generally used in *B. subtilis* and other industrial microbes for chemical production.

DETAILED DESCRIPTION

Figure 1:
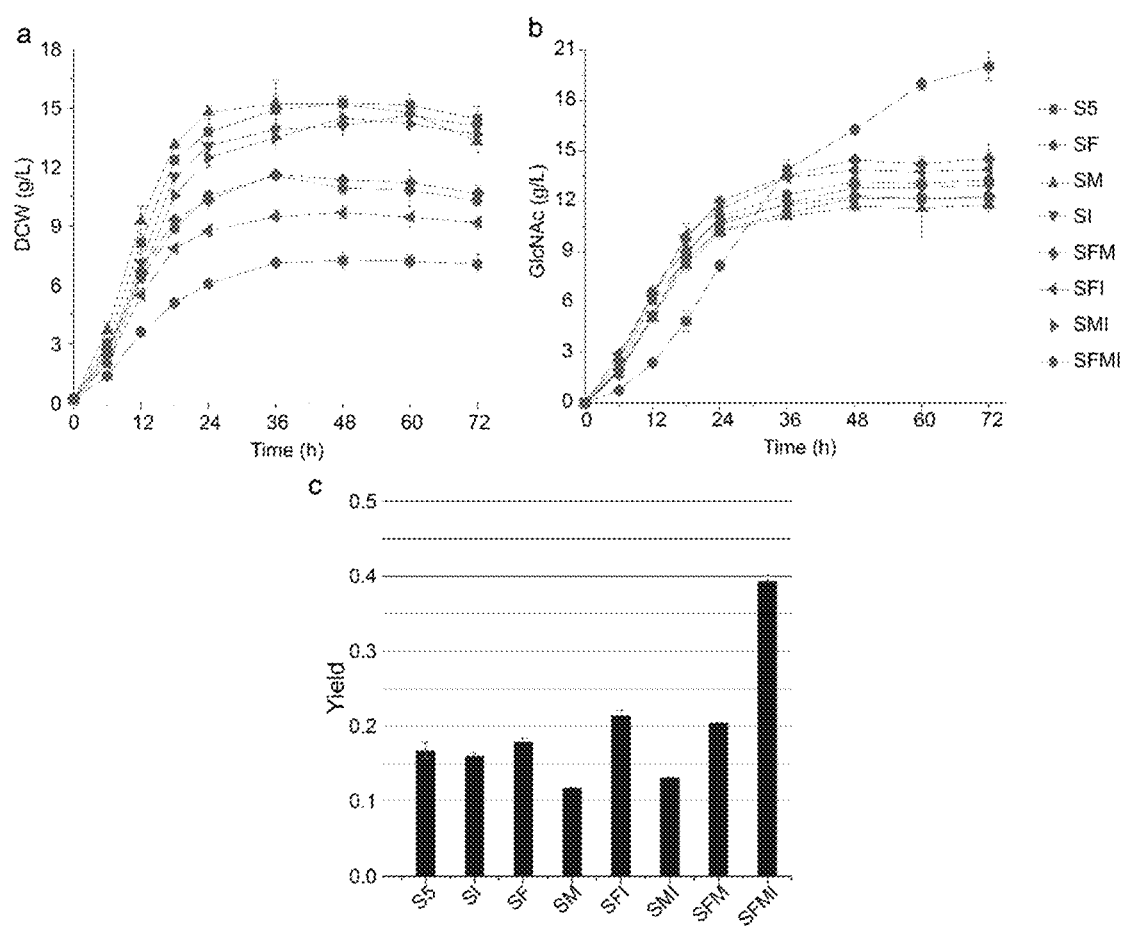
FIG. 1 shows the effects of glmS ribozyme systems regulation on cell growth and production of N-acetylglucosamine (GlcNAc). (a) cell growth, (b) GlcNAc concentration, (c) yield.

Recombinant *Bacillus subtilis* seed medium and fermentation medium:

Seed medium (g/L): tryptophan 10, yeast abstract 5, NaCl 10.

Fermentation medium (g/L): glucose 100.0, $KH_2PO_4$ 2.5, $K_2HPO_4$ 12.5, $(NH_4)_2SO_4$ 6.0, tryptophan 6.0, yeast abstract 12.0, $MgSO_4$ 3.0, and 10 mL/L trace element solution.

In one embodiment of the present invention, trace element solution comprises (g/L): $MnSO_4$ 1.0, $CoCl_2$ 0.4, $Na_2MoO_4$ 0.2, $ZnSO_4$ 0.2, $AlCl_3$ 0.1, $CuCl_2$ 0.1, Boric Acid 0.05.

Culture conditions: Seeds cultured at 37° C. and 200 rpm for 12 h were transferred into fermentation medium at 5% inoculum volume and cultured at 37° C. and 200 rpm for 72 h.

Determination of acetylglucosamine and glucosamine-6-phosphate:

The concentrations of GlcNAc, GlcN6P, were measured by high-performance liquid chromatography (HPLC) (Agilent 1260; $NH_2$ column) and a refractive index detector using 70% acetonitrile as the mobile phase at a flow rate of 0.75 mL/min and 30° C.

Determination of key enzyme activity: PFK enzyme activity determination methods was refer to the reference "Site-directed mutagenesis in *Bacillus stearothermophilus* fructose-6-phosphate 1-kinase (Journal of Biology Chemical, 264 (1989) p 131-135)"; GlmM enzyme activity determination methods was refer to the reference "Characterization of the essential gene glmM encoding phosphoglucosamine mutase in *Escherichia coli* (Journal of Biology Chemical, 271 (1996) p 32-39)"; PGI enzyme activity determination methods was refer to the reference "Model-driven redox pathway manipulation for improved isobutanol production in *Bacillus subtilis* complemented with experimental validation and metabolic profiling analysis (*PLoS One*, 9 (2014))".

Example 1 glmS Ribozyme Regulate the Expression of pfkA

The amplification primers are designed based on the up-stream and down-stream sequences of glmS ribozyme encoding gene of *Bacillus subtilis* (*Bacillus subtilis* 168, available from American Type Culture Collection, ATCC No. 27370) published in NCBI.

The up-stream primers: GlmS-F

The up-stream primers: GlmS-F
(SEQ ID NO. 2)
GCATACATTATACGAACGGTAGAGCTTGTCTTGTTCTTATTTTCTCAATA

GG;

The down-stream primers: GlmS-R
(SEQ ID NO. 3)
TTCTCCATTCACCTCAGCAACAAGATTGTAAAAGGAGACGAAGAAAGTCA

AA.

The amplification primers are designed based on the up-stream and down-stream sequences of pfkA encoding gene of *Bacillus subtilis* published in NCBI.

The up-stream homologous arm primers were:

pfk-U-F:
(SEQ ID NO. 4)
CGAACACCTGTTTACCGACTT, pfk-U-R:
(SEQ ID NO. 5)
GCTATACGAACGGTAGAATCTCCCCTCAGCAACATATATGATTAAACATA

ACA;

The down-stream homologous arm primers were:

pfk-D-F:
(SEQ ID NO. 6)
TTTGACTTTCTTCGTCTCCTTTTACAATCTTGTTGCTGAGGTGAATGGAGA

A, pfk-D-R:
(SEQ ID NO. 7)
AATACTGTGCTTCTTGCCGCGTT.

The screening marker expression cassette primers were:

spc1-F:
(SEQ ID NO. 8)
TGTTATGTTTAATCATATATGTTGCTGAGGGGAGATTCTACCGT

TCGTATAGC spc1-R:
(SEQ ID NO. 9)
CCTATTGAGAAAATAAGAACAAGACAAGCTCTACCGTTCGTATA

ATGTATGC

An up-stream homologous arm, glmS ribozyme and a down-stream homologous arm were amplified from the genome of *Bacillus subtilis* by using the above primers, and a screening marker expression cassette containing spectinomycin resistance gene was amplified from the vector PDGREF. The up-stream homologous arm, the screening marker, glmS ribozyme and the down-stream homologous arm were fused by fusion PCR technology, and an integrating cassette of glmS ribozyme encoding gene was obtained.

Example 2 glmS Ribozyme Regulate the Expression of glmM

The amplification primers are designed based on the up-stream and down-stream sequences of glmS ribozyme encoding gene of *Bacillus subtilis* (*Bacillus subtilis* 168, available from American Type Culture Collection, ATCC No. 27370) published in NCBI.

```
The up-stream primers: GlmS-F
                                            (SEQ ID NO. 10)
GCATACATTATACGAACGGTAGAGCTTGTCTTGTTCTTATTTTCTCAATA

GG;

The down-stream primers: GlmS-R
                                            (SEQ ID NO. 11)
CTTGCCCATTTTATAATCGCTTCCTCCTAAGATTGTAAGATTGTAAAAGG

AGACGAAGAA.
```

The amplification primers are designed based on the up-stream and down-stream sequences of glmM encoding gene of *Bacillus subtilis* published in NCBI.

The up-stream homologous arm primers were:

```
glm-U-F:
                                            (SEQ ID NO. 12)
AAATTGAACGGACAGGAAGCC, glm-U-R:
                                            (SEQ ID NO. 13)
CTATACGAACGGTAGAATCTCCTTATTCCGATGAGGATTGTG;
```

The down-stream homologous arm primers were:

```
glm-D-F:
                                            (SEQ ID NO. 14)
TTTGACTTTCTTCGTCTCCTTTTACAATCTTACAATCTTAGGAGGAAGCG

ATTATAAAATGGGCAAG, glm-D-R:
                                            (SEQ ID NO. 15)
CAAGACCGAGATCCGCGTTTTT.
```

The screening marker expression cassette primers were:

```
spc1-F:
                                            (SEQ ID NO. 16)
CACAATCCTCATCGGAATAAGGAGATTCTACCGTTCGTATAGC spc1-R:
                                            (SEQ ID NO. 17)
CCTATTGAGAAAATAAGAACAAGACAAGCTCTACCGTTCGTATAATGTAT

GC
```

An up-stream homologous arm, glmS ribozyme and a down-stream homologous arm were amplified from the genome of *Bacillus subtilis* by using the above primers, and a screening marker expression cassette containing spectinomycin resistance gene was amplified from the vector PDGREF. The up-stream homologous arm, the screening marker, glmS ribozyme and the down-stream homologous arm were fused by fusion PCR technology, and a integrating cassette of glmS ribozyme encoding gene was obtained.

Example 3 glmS Ribozyme Mutant Regulate the Expression of Pgi

The amplification primers are designed based on the up-stream and down-stream sequences of glmS ribozyme encoding gene of *Bacillus subtilis* (*Bacillus subtilis* 168, available from American Type Culture Collection, ATCC No. 27370) published in NCBI.

The up-stream primers: GlmS-F

```
The up-stream primers: GlmS-F
                                            (SEQ ID NO. 18)
GCATACATTATACGAACGGTAGGCTTTACCTATAATTATCCCGCCCG.

The down-stream primers: GlmS-R
                                            (SEQ ID NO. 19)
GTCATTGCTTGTCCCTCCATAACGGACTTTCAATCGTCCCCTCCTACAT

G.
```

The amplification primers are designed based on the up-stream and down-stream sequences of pgi encoding gene of *Bacillus subtilis* published in NCBI.

The up-stream homologous arm primers were:

```
pgi-U-F:
                                            (SEQ ID NO. 20)
GGTTGACATGATGAGCCACGTATTC, pgi-U-R:
                                            (SEQ ID NO. 21)
GCTATACGAACGGTAGAATCTCCCCATAACGGTATAATGTTTTCATCTTT

CACTTTAT;
```

The down-stream homologous arm primers were:

```
pgi-D-F:
                                            (SEQ ID NO. 22)
CATGTAGGAGGGGACGATTGAAAGTCCGTTATGGAGGGACAAGCAATGA

C, pgi-D-R:
                                            (SEQ ID NO. 23)
CTGACAGCAATCGGCAAGAGACCTA.
```

The screening marker expression cassette primers were:

```
spc1-F:
                                            (SEQ ID NO. 24)
ATAAAGTGAAAGATGAAAACATTATACCGTTATGGGGAGATTCTACCGTT

CGTATAGC, spc1-R:
                                            (SEQ ID NO. 25)
CGGGCGGGATAATTATAGGTAAAGCCTACCGTTCGTATAATGTATGC.
```

An up-stream homologous arm, glmS ribozyme mutant and a down-stream homologous arm were amplified from the genome of *Bacillus subtilis* by using the above primers, and a screening marker expression cassette containing spectinomycin resistance gene was amplified from the vector PDGREF. The up-stream homologous arm, the screening marker, glmS ribozyme mutant and the down-stream homologous arm were fused by fusion PCR technology, and a integrating cassette of glmS ribozyme encoding gene was obtained.

Example 4 the Construction of Recombinant *Bacillus subtilis*

The integrating cassette obtained in Example 1-3 was transformed into *Bacillus subtilis* S5 (S5-P$_{xylA}$-glmS-P$_{43}$-GNA1, short for S5), wherein the S5 is obtained by controlling recombinant expression of glmS, GNA1 by promoters of PxylA, P43 respectively, taking *B. subtilis* 168ΔnagPΔgamPΔgamAΔnagAΔnagBΔldhΔptaΔglm-S5'UTR::lox72 as a host. The construction of the strain was according to the patent application number WO/2016/015469. The correct transformants were screened and determined by PCR validation. The strains with glmS ribozyme integrated were obtained.

The positive transformant was obtained through the protocol of spectinomycin resistant plate screening, colony PCR validation. The recombinant strain SF was obtained by inserting the glmS ribozyme gene into the 5'UTR of pfkA. The recombinant strain SM was obtained by inserting the glmS ribozyme gene into the 5'UTR of glmM. The recombinant strain SI was obtained by inserting the glmS ribozyme mutant gene into the 5'UTR of pgi. The recombinant strain SFM was obtained by inserting the glmS ribozyme gene into the 5'UTR of pfkA and glmM, respectively. The recombinant strain SFI was obtained by inserting the glmS ribozyme gene into the 5'UTR of pfkA and the glmS ribozyme mutant gene into the 5'UTR of pgi, respectively. The recombinant strain SMI was obtained by inserting the glmS ribozyme gene into the 5'UTR of glmM and the glmS ribozyme mutant gene into the 5'UTR of pgi, respectively. The recombinant strain SFMI was obtained by inserting the glmS ribozyme gene into the 5'UTR of pfkA, glmM and the glmS ribozyme mutant gene into the 5'UTR of pgi, respectively.

Example 5 the Recombinant Produce Acetylglucosamie

Seeds cultured at 37° C. and 200 rpm for 12 h were transferred into fermentation medium at 5% inoculum volume at 37° C., 200 rpm for 72 h. The yield of GlcNAc of starting strain S5 reached 12.23 g/L at 72 h. The yields of GlcNAc in recombinant strain SI, SF, SM, SFI, SMI, SFM and SFMI was 12.93, 13.27, 11.79, 13.89, 12.27, 14.54, and 20.05 g/L, respectively (FIG. 1). Compared with S5, the yield of GlcNAc was increased by 63.9%.

As shown in FIG. 1, the yielding of GlcNAc of SFMI is 0.39 g/g glucose, and the GlcNAc produce reaches 20.05 g/L, yielding 2.35-fold and 1.639-fold in GlcNAC synthesis compared with that of S5. In this work, we establish a multiple setpoint dynamic control of metabolism in *B. subtilis* for the production of GlcNAc using the glmS ribozyme system.

Example 6 Activity Profiles and Intracellular GlcN6P Concentration

Seeds cultured at 37° C. and 200 rpm for 12 h were transferred into fermentation medium at 5% inoculum volume at 37° C., 200 rpm for 72 h. At 10 h, intracellular GlcN6P content and enzyme activity were analyzed.

Figure 2:
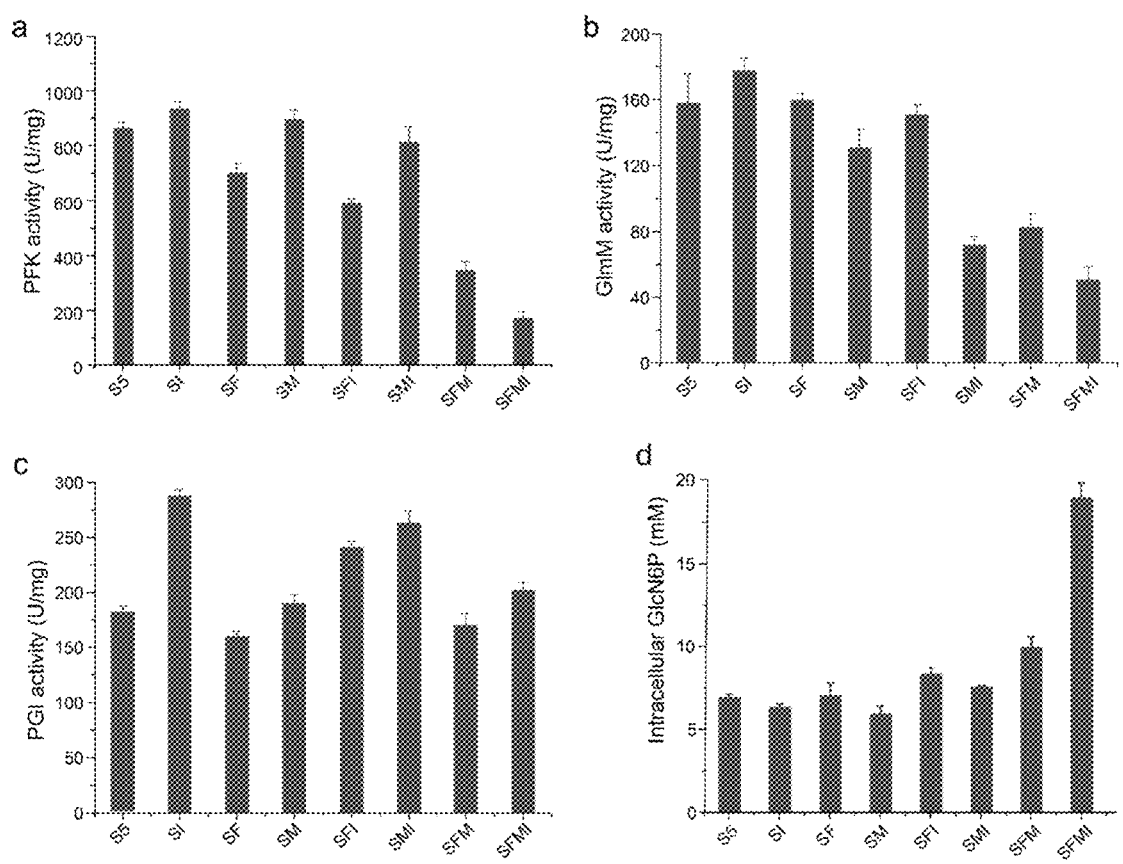
FIG. 2 shows PFK, GlmM, Pgi activities and intracellular GlcN6P concentration in crude lysates indicate the dynamic regulation. (a) PFK activities under dynamic regulation of glmS ribozyme at given times; (b) GlmM activities under dynamic regulation of glmS ribozyme at given times; (c) PGI activities under dynamic regulation of glmS ribozyme mutant at given times; (d) Intracellular GlcN6P concentrations profiles at a given time.

As shown in FIG. 2, the enzyme activities of PFK and GlmM decreased with the increasing of GlcN6P concentration, continuously. When the concentration of intracellular GlcN6P was increased from 6.9 mM to 18.9 mM, the activity of PFK decreased from 861.8 U/mg to 173.0 U/mg. Meanwhile, the activity of GlmM decreased from 157.6 U/mg to 50.6 U/mg. These shows that the concentration of intracellular GlcN6P can regulate glmS ribozyme activity, in turn glmS ribozyme regulated expression of pfkA and glmM. When glmS ribozyme mutant was inserted into the mRNA of pgi gene of SI strain, the activity of PGI increased from 180.6 U/mg to 287.6 U/mg. When glmS ribozyme mutant was inserted into the pgi gene mRNA of SFMI, PGI activity increased from 170.4 U/mg to 202.1 U/mg.

What is claimed is:

1. A recombinant strain of *Bacillus subtilis* for producing acetylglucosamine, wherein the recombinant *Bacillus subtilis* is competent to dynamically downregulate regulate glmM and pfkA and dynamically upregulate pgi expression using a glmS ribozyme and/or a glmS ribozyme mutant; wherein the recombinant *Bacillus subtilis* is constructed by homologous recombination to integrate a gene encoding glmS ribozyme into a genome of *Bacillus subtilis* between a promoter and a rbs sequence of glmM and pfkA, respectively, and integrate a gene encoding a mutant of glmS ribozyme into the genome between a promoter and a rbs sequence of pgi; wherein a sequence of the gene encoding glmS ribozyme is set forth in SEQ ID NO: 26; wherein a sequence of the gene encoding the mutant of glmS ribozyme is set forth in SEQ ID NO:1.

2. The recombinant strain of *Bacillus subtilis* of claim 1, wherein the *Bacillus subtilis* is used as a host.

3. The recombinant strain of *Bacillus subtilis* of claim 2, wherein the *Bacillus subtilis* is *Bacillus subtilis* 168, and the *Bacillus subtilis* 168 is used as a host.

4. The recombinant strain of *Bacillus subtilis* of claim 1, wherein the recombinant strain is SFMI, which is constructed by homologous recombination to integrate a gene encoding a glmS ribozyme into a genome of *Bacillus subtilis* between a promoter and a rbs sequence of glmM and pfkA, respectively, and integrate a gene encoding a mutant of glmS ribozyme into the genome between a promoter and a rbs sequence of pgi.

5. A method of making the recombinant strain of *Bacillus subtilis* of claim 1, comprising:
(1) constructing an integrating cassette of a gene encoding a glmS ribozyme, wherein the integrating cassette comprises a glmM upstream homologous fragment, a resistance gene spc, a gene fragment encoding glmS ribozyme and a glmM downstream homologous fragment; and transforming the integrating cassette into a strain of *Bacillus subtilis*, to obtain a first strain of *Bacillus subtilis* through screening and PCR validation;
(2) constructing an integrating cassette of a glmS ribozyme encoding gene, wherein the integrating cassette comprises a gene encoding a pfkA upstream homologous fragment, a resistance gene spc, a gene fragment encoding a glmS ribozyme and a pfkA downstream homologous fragment; and transforming the integrating cassette into the first strain of *Bacillus subtilis*, to obtain a second strain of *Bacillus subtilis* through screening and PCR validation;
(3) constructing an integrating cassette of a glmS ribozyme mutant encoding gene, wherein the integrating cassette comprises a pgi upstream homologous fragment, a resistance gene spc, a gene fragment encoding a glmS ribozyme mutant and a pgi downstream homologous fragment; and transforming the integrating cassette into the second strain of *Bacillus subtilis*, to obtain the recombinant strain of *Bacillus subtilis* through screening and PCR validation; wherein the gene fragment encoding the glmS ribozyme is set forth in SEQ ID NO: 26 and wherein the gene fragment encoding the glmS ribozyme mutant is set forth in SEQ ID NO: 1.

6. A method, comprising inoculating the recombinant strain of *Bacillus subtilis* of claim 1 into a fermentation medium.

7. The method of claim 6, further comprising incubating at 37° C. for 72 hours.

8. The method of claim 7, wherein the fermentation medium comprises (g/L): glucose 100.0, $KH_2PO_4$ 2.5, $K_2HPO_4$ 12.5, $(NH_4)_2SO_4$ 6.0, tryptophan 6.0, yeast abstract 12.0, $MgSO_4$ 3.0, and 10 mL/L trace element solution.

9. The method of claim 8, wherein the trace element solution comprises (g/L): $MnSO_4$ 1.0, $CoCl_2$ 0.4, $Na_2MoO_4$ 0.2, $ZnSO_4$ 0.2, $AlCl_3$ 0.1, $CuCl_2$ 0.1, Boric Acid 0.05.

* * * * *